US00PP11871P2

(12) United States Plant Patent
Fruehwirth

(10) Patent No.: US PP11,871 P2
(45) Date of Patent: May 15, 2001

(54) POINSETTIA PLANT NAMED 'ECKABSAL'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/345,569

(22) Filed: Jun. 30, 1999

(51) Int. Cl.[7] ..... A01H 3/07

(52) U.S. Cl. ..... Plt./307

(58) Field of Search ..... Plt./307, 306

(56) References Cited

PUBLICATIONS

UPOV–ROM GTIM Computer Database 2000/02, GTI Jouve Retrieval Software, citation for 'Eckabsal', Mar. 1998.*

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Poinsettia plant named 'Eckabsal', characterized by its unique dark coral pink-colored bracts that are held somewhat erect; dark green leaves; upright and spreading plant habit; very freely branching habit; strong lateral stems; and excellent postproduction longevity.

2 Drawing Sheets

BACKGROUND OF THE INVENTION

The present invention relates to a new and distinct cultivar of Poinsettia plant, botanically known as *Euphorbia pulcherrima* Willd., and hereinafter referred to by the name 'Eckabsal'.

The new Poinsettia is a product of a mutation induction breeding program conducted by the Inventor in Encinitas, Calif. The objective of the Inventor's Poinsettia development program is to create new Poinsettia cultivars having interesting bract and leaf display, desirable bract and foliage color and form, strong and freely branching stems and good post-production longevity.

The new Poinsettia originated by exposing unrooted cuttings of the commercial *Euphorbia pulcherrima* Willd. cultivar '559', disclosed in U.S. Plant Pat. No. 8,773, to gamma-ray radiation at a level of 3,000 rads. The new Poinsettia was discovered and selected by the Inventor in 1996. The selection of this plant was based on its unique bract color.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristicsof 'Eckabsal'. These characteristics in combination distinguish 'Eckabsal' as a new and distinct cultivar:

1. Unique dark coral pink-colored bracts that are held somewhat erect.

2. Dark green leaves.

3. Upright and spreading plant habit.

4. Very freely branching habit; strong lateral stems.

5. Excellent postproduction longevity.

In side-by-side comparisons conducted by the Inventor in Encinitas, Calif., plants of the new Poinsettia differed from plants of parent cultivar, '559', primarily in bract coloration as bracts of plants of '559' are red. Additionally plants of the new Poinsettia and '559' have been noted to be different in the following characteristics:

1. Plants of the new Poinsettia are more freely branching than plants of '559'.

2. Bracts of plants of the new Poinsettia are slightly shorter, narrower and more pointed than bracts of plants of '559'.

3. Plants of the new Poinsettia flower later than plants of the cultivar '559'.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type.

The photograph on the first sheet comprises a side perspective view of a typical plant of 'Eckabsal'.

The photograph at the top of the second sheet comprises a top perspective view of a typical plant of 'Eckabsal'.

The photograph at the bottom of the second sheet is a close-up view of typical bracts and leaves of 'Eckabsal' (left) and '559' (right).

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a polyethylene-covered greenhouse with day temperatures about 22 to 24° C., night temperatues about 16 to 18° C., and light levels about 4,000 foot-candles. Plants were grown in 16.5-cm pots, pinched one time, and flowered under naturally lengthening nights during the fall/early winter.

In the following description, color references are made to The Royal Horticultural Society Colour Chart except where general terms of ordinary dictionary significance are used.

Botanical Classification: *Eurphorbia pulcherrima* Willd. 'Eckabsal'.

Parentage: Induced mutation of *Eurphorbia pulcherrima* Willd. cultivar '559', disclosed in U.S. Plant Pat. No. 8,773.

Propagation:

*Type cutting.*—Terminal cuttings.

*Time to initiate roots.*—Summer: About 12 to 18 days at 26 to 28° C. Winter: About 15 to 18 days at 24° C.

*Time to develop roots.*—Summer: About 26 days at 26 28° C. Winter: About 26 days at 24° C.

*Rooting habit.*—Thick, freely branching, becoming fibrous with development.

Plant description:

*Plant form.*—Wide inverted triangle, top of plant rounded.

*Growth habit.*—Upright and spreading. Very freely branching. Branching is enhanced by removing the shoot apex.

*Plant vigor.*—Moderate.

*Plant height.*—About 30 cm.

*Crop time.*—From unrooted cuttings to a flowering plant in a 16.5-cm container, about 18 weeks are required.

*Stem description.*—Number of lateral branches: About eight lateral branches are formed after removal of the terminal apex. Lateral branch length: About 22 cm. Internode length: About 1.25 cm. Stem color: 146A to 146B.

*Foliage description.*—Quantity of leaves per lateral branch: About 8. Length: About 12 cm. Width: About 7.5 cm. Shape: Mostly ovate with irregularly rounded lobes. Apex: Acuminate. Base: Acute. Margin: Entire. Texture: Smooth. Mostly glabrous with very slight pubescence on lower surface. Color: Young foliage, upper surface: 147A. Young foliage, lower surface: 146C. Mature foliage, upper surface: 147A. Mature foliage, lower surface: 146B to 146C. Venation, upper surface: 147B. Venation, lower surface: 147C. Petiole: Length: About 5.5 cm. Diameter: About 3 mm. Color: 59C.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long night conditions. Response time is about 9.5 weeks.

*Quantity of inflorescences.*—One per lateral branch, usually about eight per plant.

*Inflorescence size.*—Diameter: About 27 cm. Height (depth): About 5 cm.

*Flower bracts.*—Quantity of flower bracts per inflorescence: Usually about 15 primary bracts and about 7 smaller secondary bracts per inflorescence. Length, largest bracts: About 16 cm. Width, largest bracts: About 7.5 cm. Shape: Mostly ovate or with irregular rounded lobes. Apex: Acuminate. Base: Acute. Margin: Entire. Texture: Smooth. Aspect: Somewhat erect. Color: Developing, upper surface: 47B. Developing, lower surface: 47C. Mature, upper surface: 50A; color does not fade. Mature, lower surface: 50B to 50C.

*Cyathia.*—Quantity: Usually about 10 per corymb. Diameter of cyathia cluster: Very tight, about 2 cm. Length: About 1 cm. Width: About 5 mm. Color: Immature: 144B. Mature: 144A to 144B. Peduncle: Length: About 3 mm. Aspect: Strong, erect. Color: 144C. Stamens: Stamen number: Very numerous, typically more than 20 per cyathium. Anther size: Less than 1 mm. Anther shape: Oval. Anther color: 46A. Amount of pollen: Moderate. Pollen color: 7B. Pistils: No pistillate flowers observed. Nectary color: 14A to 14B.

Disease resistance: No fungal, bacterial nor viral problems observed on plants grown under commercial conditions.

Postproduction longevity: Generally plants maintain good substance and bract color for about six weeks under interior conditions.

It is claimed:

1. A new and distinct cultivar of Poinsettia named 'Eckabsal', as illustrated and described.

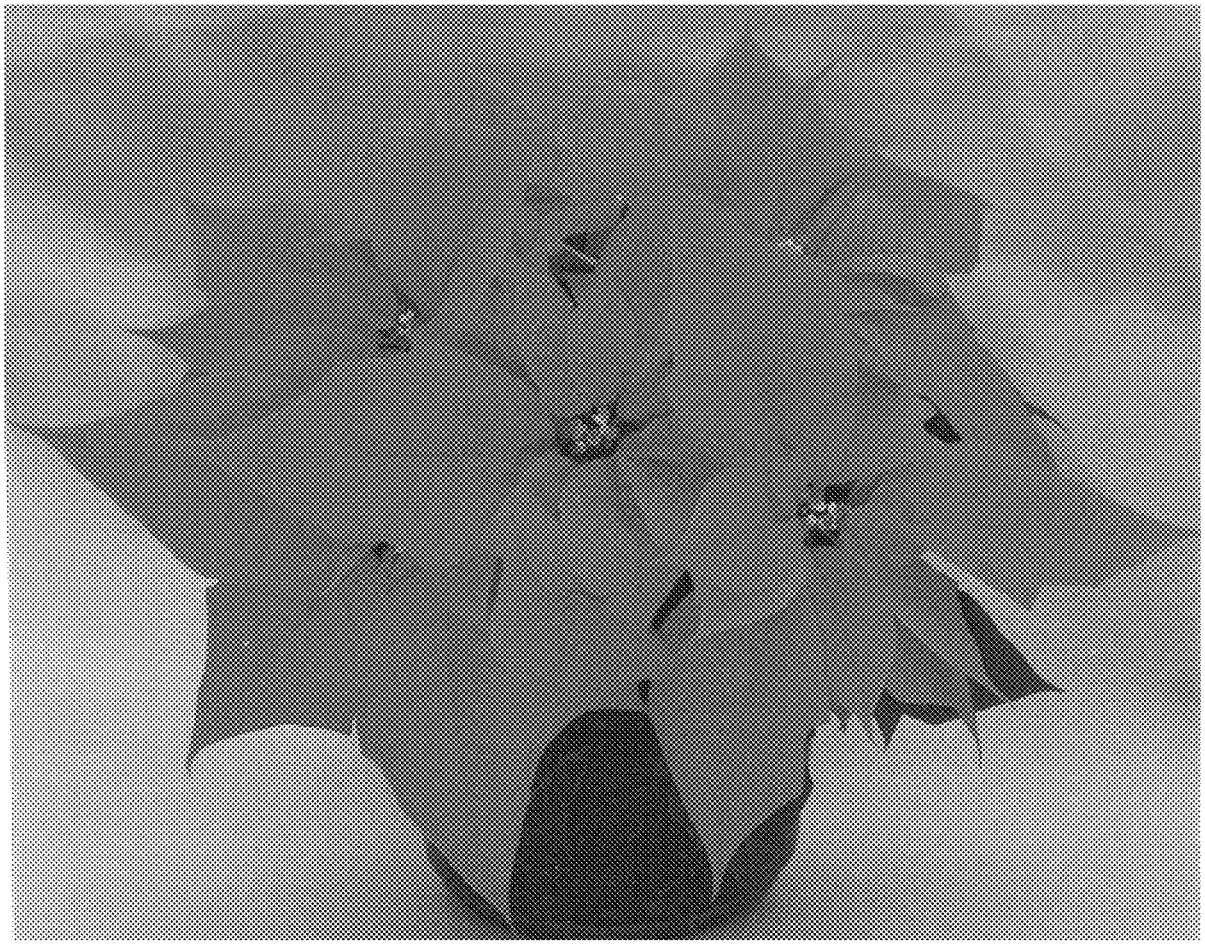

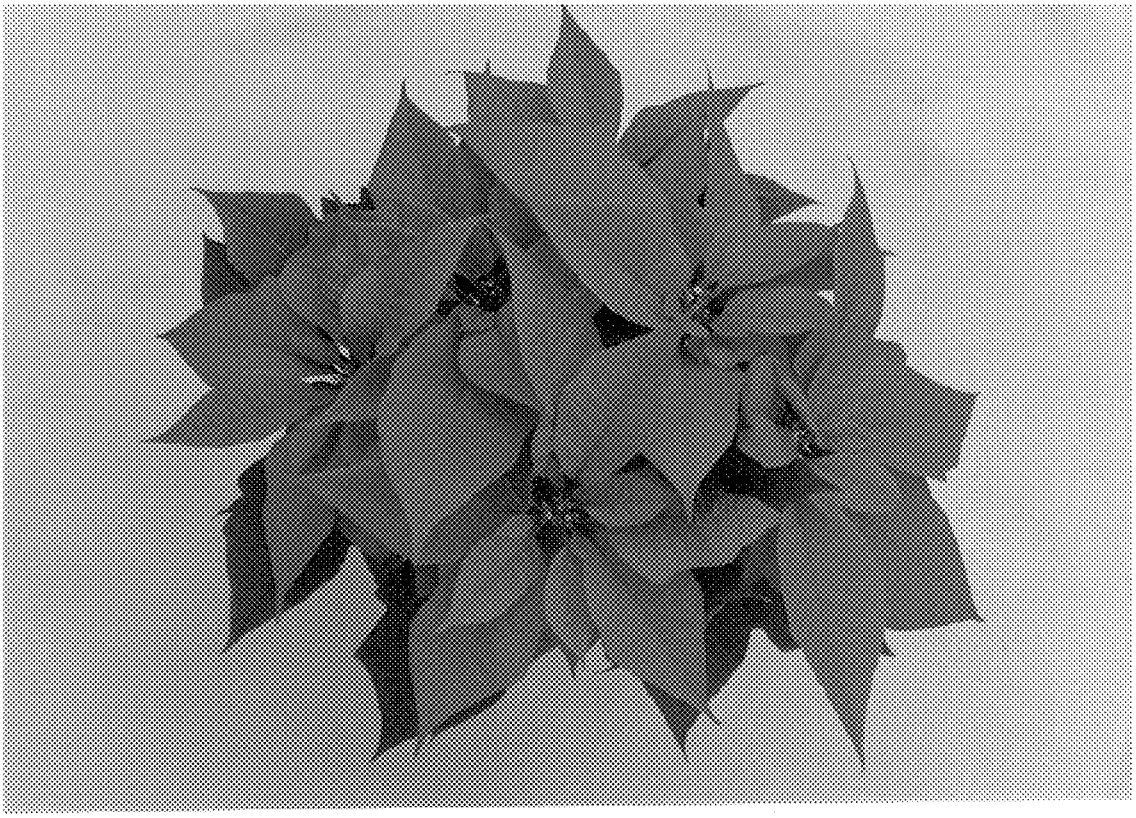
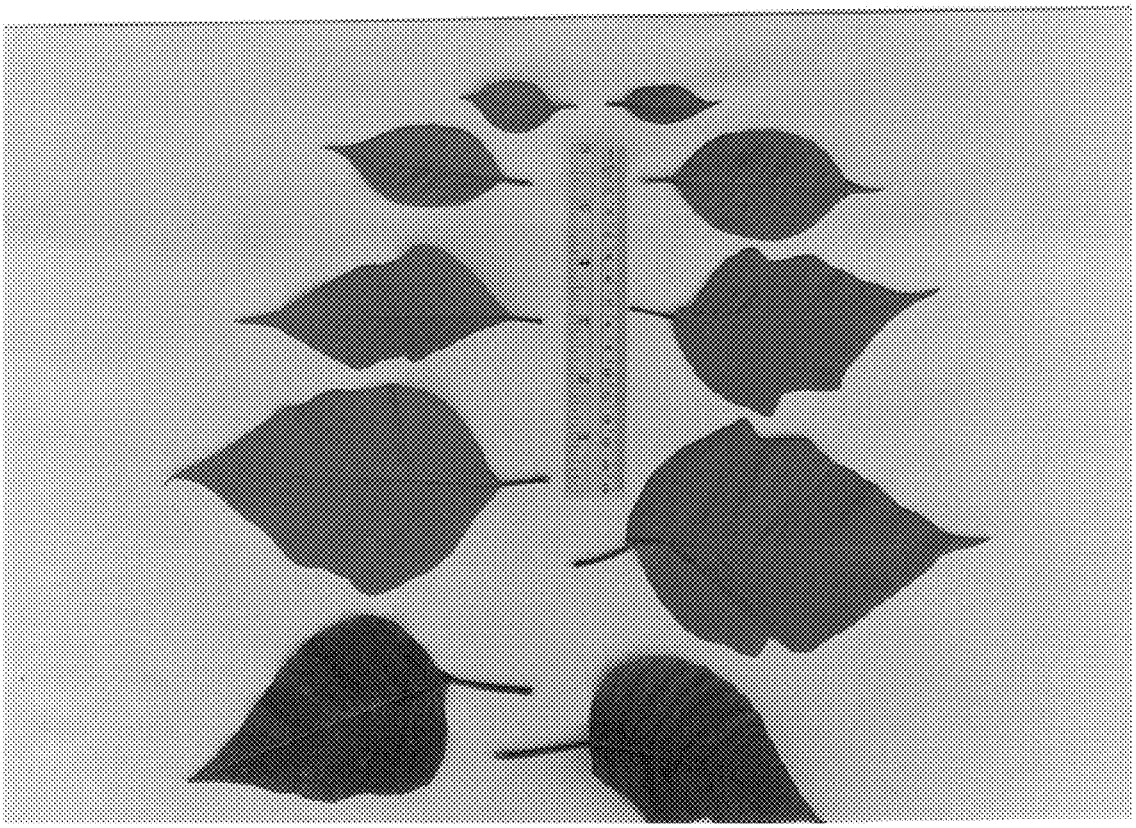

* * * * *